United States Patent [19]

Taniuchi et al.

[11] Patent Number: 5,072,000

[45] Date of Patent: Dec. 10, 1991

[54] METHOD OF PRODUCING IMIDE BOND-CONTAINING COMPOUNDS AND FLAME RETARDANTS COMPRISING SUCH COMPOUNDS

[75] Inventors: Akira Taniuchi; Hirohito Komori; Koichi Niwa, all of Kyoto, Japan

[73] Assignee: Dai-Ichi Kogyo Seiyaku Co., Ltd., Kyoto, Japan

[21] Appl. No.: 300,630

[22] Filed: Jan. 23, 1989

[30] Foreign Application Priority Data

Feb. 3, 1988 [JP] Japan ................................ 63-24811

[51] Int. Cl.$^5$ .......................................... C07D 209/48
[52] U.S. Cl. .................................. 548/462; 548/520; 548/523; 524/94
[58] Field of Search ............... 548/673, 462, 520, 523, 548/524; 528/48; 525/439

[56] References Cited

U.S. PATENT DOCUMENTS

| | | | |
|---|---|---|---|
| 3,300,420 | 1/1967 | Frey | 521/157 |
| 3,624,024 | 11/1971 | Caldwell | 558/274 |
| 3,701,756 | 10/1972 | Carleton et al. | 528/48 |
| 4,137,221 | 1/1979 | Hara et al. | 525/439 |
| 4,220,563 | 9/1980 | Hara et al. | 525/439 |
| 4,251,649 | 2/1981 | Hara et al. | 525/439 |
| 4,296,218 | 10/1981 | Hara et al. | 525/439 |

FOREIGN PATENT DOCUMENTS 1951632 5/1971 Fed. Rep. of Germany .

OTHER PUBLICATIONS

Musaeva et al., "Kinetics and mechanism . . . ", CA 103(17) 141179x (1985).
Oksent'evich et al., "Thermal properties of . . . ", CA 101(10): 73567d (1984).

Primary Examiner—C. Warren Ivy
Assistant Examiner—Celia Chang
Attorney, Agent, or Firm—Jordan and Hamburg

[57] ABSTRACT

The invention relates to a method of producing imide bond-containing compounds and flame retardants comprising such compounds. The method comprises reacting an acid anhydride with an isocyanate compound in an inert solvent in the presence of a tertiary amine as catalyst. The imide bond-containing compounds thus obtained provide flammable substances with good flame resistance and at the same time themselves have good heat resistance and weather resistance. Therefore, the flame retardants comprising such compounds have a wide field of application.

2 Claims, No Drawings

METHOD OF PRODUCING IMIDE BOND-CONTAINING COMPOUNDS AND FLAME RETARDANTS COMPRISING SUCH COMPOUNDS

BACKGROUND OF THE INVENTION

This invention relates to a method of producing imide bond-containing compounds and flame retardants comprising such compounds.

Recent years have seen a constant and remarkable expansion of the field of applications of plastics. The characteristics required of plastic materials have become diversified accordingly. In particular, flame resistance is a characteristic required of plastics to be used in a very great number of applications, for example as building materials, materials for electric appliances, and automobile parts, among others. The role of flame retardants, or fire retardants, which provide plastics with fire and flame resistance, is very important.

Such flame retardants are required not only to be able to provide plastics with good flame resistance without impairing the intrinsic physical properties of the plastics but also to have, by themselves, good heat resistance and weather resistance.

Under such circumstances, certain flame retardants comprising imide bond-containing compounds have attracted recent attention but are not fully satisfactory as yet.

SUMMARY OF THE INVENTION

Accordingly, it is an object of the invention to provide a method of producing imide bond-containing compounds not only capable of providing plastics with good flame resistance without impairing the physical properties of the plastics but also themselves having good heat resistance and weather resistance. A further object is to provide flame retardants comprising such compounds.

The invention thus provides a method of producing imide bond-containing compounds of the general formula

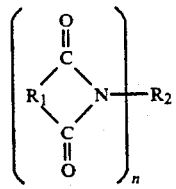
(3)

wherein $R_1$ is a Br—, Cl—, F— or I-containing aromatic or alicyclic nucleus, $R_2$ is an aliphatic, aromatic or alicyclic hydrocarbon residue, and n is an integer of 1 to 4, which comprises reacting an acid anhydride of the general formula

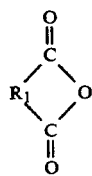
(1)

wherein $R_1$ is as defined above, with an isocyanate compound of the general formula $$R_2(NCO)_n \quad (2)$$

wherein $R_2$ and n are as defined above, in an inert solvent in the presence of a tertiary amine as catalyst as well as flame retardants comprising such compounds.

DETAILED DESCRIPTION OF PREFERRED EMBODIMENTS

As the acid anhyride of general formula (1) to be used in the practice of the invention, there may be mentioned, for example, tetrachlorophthalic anhydride, tetrabromophthalic anhydride, tetrafluorophthalic anhydride, tetraiodophthalic anhydride, dibromotetrahydrophthalic anhydride, dichlorotetrahydrophthalic anhydride, chlorendic anhydride, bromendic anhydride, dibromophthalic anhydride and dichlorophthalic anhydride.

As the isocyanate compound of general formula (2), there may be mentioned, for example, 1,6-hexamethylene diisocyanate, tolylene diisocyanate, diphenylmethanediisocyanate, isophorone diisocyanate, phenyl isocyanate, dianisidine diisocyanate, hydrogenated diphenylmethanediisocyanate, p-chlorophenyl isocyanate, dichlorophenyl isocyanate, ethyl isocyanate, triphenylmethanetriisocyanate, trimethylenetetraphenyl isocyanate, hydrogenated tolylene diisocyanate, xylenediisocyanate, polymethylenepolyphenyl isocyanate and the like.

As the tertiary amine to be used as catalyst, there may be mentioned, for example, triethylamine, tributylamine, dimethylaniline, triallylamine, trioctylamine, dimethylbenzylamine, lauryldimethylamine, pyridine and picoline.

As the inert solvent to be used in the practice of the invention, there may be mentioned, for example, xylene, toluene, dimethylformamide, dimethylacetamide, benzene, cyclohexane and dimethyl sulfoxide. These solvents may be used as a mixture of two or more of them.

The method of producing imide bond-containing compounds of general formula (3) as provided by the present invention consists in reacting the abovementioned acid anhydride of general formula (1) with the above-mentioned isocyanate compound of general formula (2) in such inert solvent in the presence, as catalyst, of a tertiary amine such as mentioned above.

The reaction involved in the inventive method may be illustrated as follows:

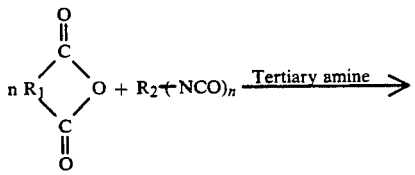

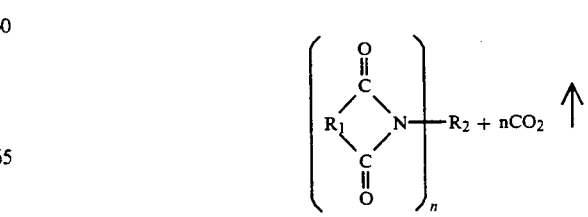

In carrying out the above reaction, it is preferable to use the acid anhydride of general formula (1) in an amount of 1 to 1.1 moles per 1/n mole of the isocyanate compound of general formula (2).

The tertiary amine, which is to be used as catalyst, is preferably used in an amount of 0.01 to 10% by weight based on the sum total of the acid anhydride of general formula (1) and the isocyanate compound of general formula (2). In carrying out the reaction, the inert solvent is used preferably in an amount of 1 to 10 times the sum total of the acid anhydride of general formula (1) and the isocyanate compound of general formula (2).

According to a more specific example of the reaction procedure, the acid anhydride of general formula (1) is dissolved in the inert solvent, then the catalyst tertiary amine is added to the solution and, thereafter, the isocyanate compound of general formula (2) is added dropwise to the solution. The reaction is preferably carried out at a temperature of 50°-150° C. for a period of 3-10 hours.

The flame retardants according to the invention each contain, as a flame retardant component, the imide bond-containing compound of general formula (3) as obtained in the above manner.

The flame retardants according to the invention are excellent additive-type flame retardants for use in general-purpose synthetic resins, such as polystyrene resins, polyethylene resins, polypropylene resins, acrylic resins, vinyl chloride resins, saturated or unsaturated polyester resins, melamine resins, epoxy resins and phenol resins, as well as in engineering plastics, such as ABS resins, polyphenylene oxide resins, polycarbonate resins and polyamide resins. They are also suited for use in the aqueous dispersion form in treating fibers, papers, rubbers and so forth for providing them with flame resistance.

The flame retardants according to the invention, when used in combination with conventional halogen-containing flame retardants and/or phosphorus-containing flame retardants; flame retardant resins, such as brominated epoxy resins, polybrominated styrene resins, phosphorus-containing polyesters and chlorinated polyethylene; auxiliary flame retardants, such as antimony trioxide; and so forth, can produce much better flame retarding effects.

Furthermore, the flame retardants according to the invention may be used in combination with antioxidants, ultraviolet absorbers, infrared absorbers, antistatic agents, inorganic fillers, solvents, plasticizers, nucleating agents, pigments and the like.

The level of addition of the flame retardants according to the invention should be selected suitably depending on the kind of material to which they are added. Generally, however, said flame retardants are preferably used in an amount of 0.2-30% by weight. The method of addition is optional. For example, the flame retardants according to the invention are added to materials, either as such or in the form of a solution in a solvent or of a dispersion or emulsion in water or an oil.

The production method according to the invention gives the imide bond-containing compounds of general formula (3) in high yields. Furthermore, the imide bond-containing compounds of general formula (3) as provided by the invention can provide flammable substances with good flame resistance and at the same time they themselves have remarkable heat resistance and good weather resistance. Therefore, the flame retardants comprising such compounds can be used in a wide field.

The following examples and comparative examples illustrate the invention in further detail. It is to be noted, however, that such examples are by no means limitative of the scope of the invention.

Example 1

A four-necked flask equipped with a stirrer, a cooling condenser, a thermometer and a dropping funnel was charged with 92.8 g of tetrabromophthalic anhydride, 200 g of xylene and 100 g of dimethylformamide, and the mixture was stirred with heating at 80° C. After dissolution of the contents, 3 g of triethylamine was added. Then, 16.8 g of hexamethylene diisocyanate was added dropwise from the dropping funnel. After completion of the dropping, the flask contents were heated at 120° C. for 8 hours and, then, the solvents were distilled off under reduced pressure. The remaining reaction product was washed with warm water (80° C.). This product was further washed with a mixture of 200 ml of water and 20 g of 28% aqueous ammonia, collected by filtration, washed with water and dried. Thus was obtained 91 g (yield 90.0%) of the desired, imide bond-containing compound having a structure such that, in general formula (3),

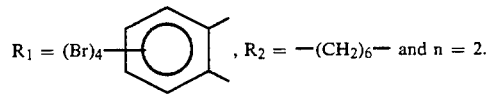

$R_1 = (Br)_4$ , $R_2 = -(CH_2)_6-$ and $n = 2$.

The elemental analysis and DTA (differential thermal analysis) data obtained with the above compound are shown below.

Elemental analysis:
Br %: 64.3 (64.0)
N %: 2.7 (2.8)
C %: 26.8 (26.4)
O %: 6.5 (6.4)
H %: 1.2 (1.2)

Hereinabove and hereinafter, the numerical values in the parentheses are calculated values, as far as elemental analysis data are concerned.

DTA analysis:
10% weight loss: 384° C.
50% weight loss: 416° C.

EXAMPLE 2

The same reaction apparatus as used in Example 1 was charged with 74.2 g of HET anhydride (chlorendic anhydride), 200 g of xylene and 200 g of dimethylformamide, and the mixture was heated at 80°-90° C. After dissolution of the contents, 5 g of tributylamine was added. Then, 16.8 g of hexamethylene diisocyanate was added dropwise. After completion of the dropping, the reaction was conducted at 120°-130° C. for 6 hours. Thereafter, the solvents were distilled off under reduced pressure. The remaining reaction product was washed with 200 ml of acetone and dried. Thus was obtained 78.5 g (yield 95.5%) of the desired, imide bond-containing compound having a structure such that, in general formula (3),

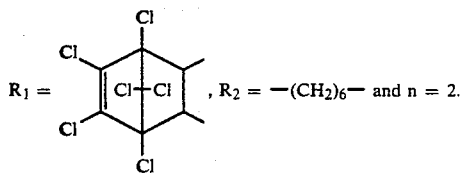, $R_2 = -(CH_2)_6-$ and n = 2.

The elemental analysis and DTA data obtained with the above compound are shown below.
Elemental analysis:
Cl %: 52.10 (51.80)
N %: 2.85 (2.92)
C %: 34.61 (35.00)
O %: 7.71 (7.79)
H %: 1.25 (1.21)
DTA analysis:
10% weight loss: 335° C.
50% weight loss: 460° C.

EXAMPLE 3

The same apparatus as used in Example 1 was charged with 92.8 g of tetrabromophthalic anhydride, 200 g of xylene and 100 g of dimethylacetamide. After nitrogen gas substitution of the system, the flask contents were heated at 70° C. After dissolution of the contents, 3.5 g of triethylamine was added. Then, 25.8 g of hydrogenated diphenylmethanediisocyanate was added dropwise from the dropping funnel. After completion of the dropping, the reaction was conducted at 125°-130° C. for 10 hours. Thereafter, the solvents were distilled off. The remaining reaction product was washed with warm water (60° C.) and collected by filtration. The product was then washed with 400 g of 2% aqueous sodium hydroxide solution, collected by filtration, washed with water and dried. Thus was obtained 98.6 g (yield 89.8%) of the desired, imide bond-containing compound having a structure such that, in general formula (3),

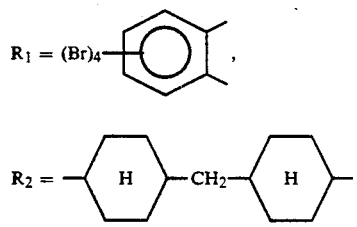

and n=2.

The elemental analysis and DTA data obtained with the above compound are shown below.
Elemental analysis:
Br%: 59.00 (58.31)
N %: 2.51 (2.55)
C %: 31.20 (31.69)
O %: 5.78 (5.82)
H %: 1.98 (2.00)
DTA analysis:
10% weight loss: 313° C.
50% weight loss: 370° C.

EXAMPLE 4

The same apparatus as used in Example 1 was charged with 92.8 g of tetrabromophthalic anhydride, 210 g of xylene and 90 g of dimethylformamide, and the mixture was heated at 80° C. for dissolution. Thereafter, 2 g of dimethylbenzylamine was added and then 12.4 g of 2,6-tolylene diisocyanate was added dropwise from the dropping funnel. After completion of the dropping, the reaction was conducted at 125°-130° C. for 8 hours and then the solvents were distilled off. The remaining reaction product was washed twice with warm water (50° C.), then with 5% aqueous ammonia and further with water and dried. Thus was obtained 88.8 g (yield 92.1%) of the desired, imide bond-containing compound having a structure such that, in general formula (3),

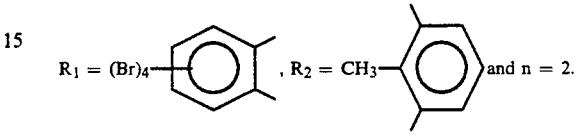

The elemental analysis and DTA data obtained with the above compound are shown below.
Elemental analysis:
Br%: 66.10 (66.39)
N %: 2.87 (2.90)
C %: 28.70 (28.63)
O %: 6.66 (6.64)
H %: 0.60 (0.62)
DTA analysis:
10% weight loss: 365° C.
50% weight loss: 500° C.

COMPARATIVE EXAMPLE 1

The same apparatus as used in Example 1 was charged with 92.8 g of tetrabromophthalic anhydride, 200 g of xylene and 100 g of dimethylformamide, and the mixture was heated at 80° C. for dissolution. Then, 11.6 g of hexamethylenediamine was added, and the whole mixture was stirred for 6 hours with heating at 130°-140° C. During this period, 4.0 g of distillate water was removed by trapping. The solvents were then distilled off under reduced pressure. The remaining reaction product was washed with 300 ml of methanol, collected by filtration, further washed with a mixture of 200 ml of water and 20 g of 28% aqueous ammonia and then with water, collected by filtration and dried. Thus was obtained 88 g (yield 88%) of an imide bond-containing compound. Elemental analysis and DTA of this compound gave the data shown below. This data confirmed that the compound obtained in this comparative example was identical with the compound obtained in Example 1.
Elemental analysis:
Br%: 64.1 (64.0)
N %: 2.5 (2.8)
C %: 26.6 (26.4)
O %: 6.3 (6.4)
H %: 1.1 (1.2)
DTA analysis:
10% weight loss: 398° C.
50% weight loss: 420° C.

EXAMPLE 5

High impact polystyrene (Nippon Steel Chemical's ESTYRENE® H65; 100 parts by weight) and 20 parts by weight of the imide bond-containing compound obtained in Example 1 were kneaded together on a hot roll mill at 200° C. for 5 minutes and the mixture was hot-pressed at 210° C. for 2 minutes for molding. Specimens, 1/16 inch in thickness, were prepared from the molding in accordance with UL 94 (Underwriters Laboratories Inc. Standard for Tests for Flammability of Plastic Materials), and the burning test was performed.

The duration of flaming (duration of burning with flaming combustion) was 18.0 seconds and the duration of glowing (duration of glowing combustion without flaming) was 1.6 seconds, hence the molding was classed 94V-2 according to UL 94. Slight dripping was observed.

EXAMPLE 6

A mixture of 100 parts by weight of the same high impact polystyrene as used in Example 5, 15 parts by weight of one of the imide bond-containing compounds obtained in Examples 1–4 and Comparative Example 1, and 5 parts by weight of antimony trioxide was kneaded and molded in the same manner as in Example 5, and the molding was tested for flammability in the same manner as in Example 5. The results thus obtained are shown below.

| Imide bond-containing compound used | Duration of flaming (seconds) | Duration of glowing (seconds) | UL 94 |
| --- | --- | --- | --- |
| Example 1 | 4.2 | 2.0 | Classed V-0 |
| Example 2 | 16.5 | 3.0 | Classed V-0 |
| Example 3 | 6.4 | 3.5 | Classed V-0 |
| Example 4 | 3.6 | 1.8 | Classed V-0 |
| Comparative Example 1 | 4.2 | 2.8 | Classed V-0 |

No dripping was observed in any case.

We claim:
1. A compound of the formula

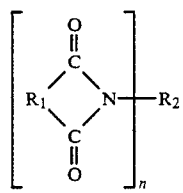

wherein

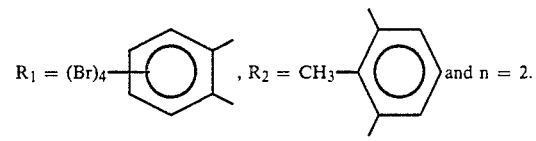

$R_1 = (Br)_4$—, $R_2 = CH_3$— and $n = 2$.

2. A flame retardant comprising the compound of claim 1.

* * * * *